US010950351B2

(12) United States Patent
Madabhushi et al.

(10) Patent No.: US 10,950,351 B2
(45) Date of Patent: Mar. 16, 2021

(54) METHODS AND APPARATUS FOR PREDICTING BENEFIT FROM IMMUNOTHERAPY USING TUMORAL AND PERITUMORAL RADIOMIC FEATURES

(71) Applicant: Case Western Reserve University, Cleveland, OH (US)

(72) Inventors: Anant Madabhushi, Shaker Heights, OH (US); Mahdi Orooji, Cleveland, OH (US); Niha Beig, Cleveland Heights, OH (US); Vamsidhar Velcheti, Pepper Pike, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 66 days.

(21) Appl. No.: 16/251,214

(22) Filed: Jan. 18, 2019

(65) Prior Publication Data
US 2019/0156954 A1    May 23, 2019

Related U.S. Application Data

(63) Continuation of application No. PCT/US2017/041330, filed on Jul. 10, 2017.
(Continued)

(51) Int. Cl.
*G16H 50/30*    (2018.01)
*G16H 50/50*    (2018.01)
(Continued)

(52) U.S. Cl.
CPC .......... *G16H 50/30* (2018.01); *G06K 9/0014* (2013.01); *G06K 9/00026* (2013.01);
(Continued)

(58) Field of Classification Search
CPC ........ G16H 50/30; G16H 50/50; G16H 30/20; G16H 50/20; G16H 30/40; G16B 50/30;
(Continued)

(56) References Cited

U.S. PATENT DOCUMENTS

| | | | |
|---|---|---|---|
| 2014/0024553 A1* | 1/2014 | Michalek | G16H 50/70 506/9 |
| 2014/0301619 A1* | 10/2014 | Stavros | A61B 8/5223 382/131 |

(Continued)

OTHER PUBLICATIONS

Depeursinge et al. "Three-Dimensional Solid Texture Analysis in Biomedical Imaging: Review and Opportunities." Medical Image Analysis 18 (2014) 176-196. Published on Oct. 22, 2013.
(Continued)

*Primary Examiner* — Leon Viet Q Nguyen
(74) *Attorney, Agent, or Firm* — Eschweiler & Potashnik, LLC

(57) ABSTRACT

Methods, apparatus, and other embodiments predict response to immunotherapy from computed tomography (CT) images of a region of tissue demonstrating non-small cell lung cancer (NSCLC). One example apparatus includes a set of circuits that includes an image acquisition circuit that accesses a CT image of a region of tissue demonstrating cancerous pathology, a tumoral definition circuit that generates a tumoral surface boundary that defines a tumoral volume, a peritumoral segmentation circuit that generates a peritumoral region based on the tumoral surface boundary, and that segments the peritumoral region into a plurality of annular bands, a radiomics circuit that extracts a set of discriminative features from the tumoral volume and at least one of the plurality of annular bands, and a classification circuit that classifies the ROI as a responder or a non-responder, based, at least in part, on the set of discriminative features.

19 Claims, 8 Drawing Sheets

Related U.S. Application Data

(60) Provisional application No. 62/365,774, filed on Jul. 22, 2016.

(51) Int. Cl.

| | | |
|---|---|---|
| *G16H 50/20* | (2018.01) | |
| *G16H 30/20* | (2018.01) | |
| *G16H 30/40* | (2018.01) | |
| *G16B 50/30* | (2019.01) | |
| *G16B 40/10* | (2019.01) | |
| *G06K 9/00* | (2006.01) | |
| *G06T 7/00* | (2017.01) | |
| *G06T 11/00* | (2006.01) | |

(52) U.S. Cl.
CPC .......... *G06T 7/0012* (2013.01); *G06T 11/003* (2013.01); *G16B 40/10* (2019.02); *G16B 50/30* (2019.02); *G16H 30/20* (2018.01); *G16H 30/40* (2018.01); *G16H 50/20* (2018.01); *G16H 50/50* (2018.01); *G06T 2207/10081* (2013.01); *G06T 2207/30061* (2013.01)

(58) Field of Classification Search
CPC .. G16B 40/10; G06K 9/00026; G06K 9/0014; G06K 9/6256; G06K 9/6284; G06T 11/003; G06T 2207/10081; G06T 2207/30061; G06T 7/0016; G06T 7/11; G06T 7/0012; G01N 15/14; G01N 15/1475

See application file for complete search history.

(56) References Cited

U.S. PATENT DOCUMENTS

| | | |
|---|---|---|
| 2016/0155225 A1 | 6/2016 | Madabhushi et al. |
| 2016/0203599 A1* | 7/2016 | Gillies .................. A61B 6/463 382/132 |

OTHER PUBLICATIONS

Ganeshan et al. "Quantifying Tumour Heterogeneity With CT." Cancer Imaging (2013) 13(1), 140-149. Published in 2013.

Sundar et al. "Nivolumab in NSCLC: Latest Evidence and Clinical Potential." Therapeutic Advances in Medical Oncology, 2015, vol. 7(2) 85-96. Published in 2015.

International Search Report & Written Opinion of the International Searching Authority dated Oct. 12, 2017 for International Application No. PCT/US2017/041330.

\* cited by examiner

METHODS AND APPARATUS FOR PREDICTING BENEFIT FROM IMMUNOTHERAPY USING TUMORAL AND PERITUMORAL RADIOMIC FEATURES

REFERENCE TO RELATED APPLICATIONS

This Application is a Continuation of International Application number PCT/US2017/041330, filed on Jul. 10, 2017, which claims priority to U.S. Provisional Application No. 62/365,774, filed on Jul. 22, 2016. The contents of the above-referenced patent applications are hereby incorporated by reference in their entirety.

BACKGROUND

Lung cancer is the world's leading cause of cancer death. Nearly two million patients are diagnosed with lung cancer every year, and approximately 1.7 million lung cancer related deaths occur every year globally. Non-small cell lung cancer (NSCLC) is the leading cause of cancer related mortality worldwide. Platinum based cytotoxic chemotherapy is one approach to treating NSCLC. However, first-line platinum based cytotoxic chemotherapy for advanced NSCLC produces transient responses at best, possibly because tumor protein p53-system mutation or deletion is universal in NSCLC and metastatic disease.

The immune checkpoint inhibitor anti programmed death-1 (PD-1) nivolumab, has been employed in second-line treatment for NSCLC as an immunotherapy for NSCLC. Nivolumab has an excellent toxicity profile and may induce durable, clinically meaningful responses. However, the objective response rate to nivolumab is only approximately 20%: only about 20% of NSCLC patients respond to nivolumab. Furthermore, conventional tissue based markers for predicting patient response to nivolumab are ineffective.

BRIEF DESCRIPTION OF THE DRAWINGS

The accompanying drawings, which are incorporated in and constitute a part of the specification, illustrate examples of apparatus, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
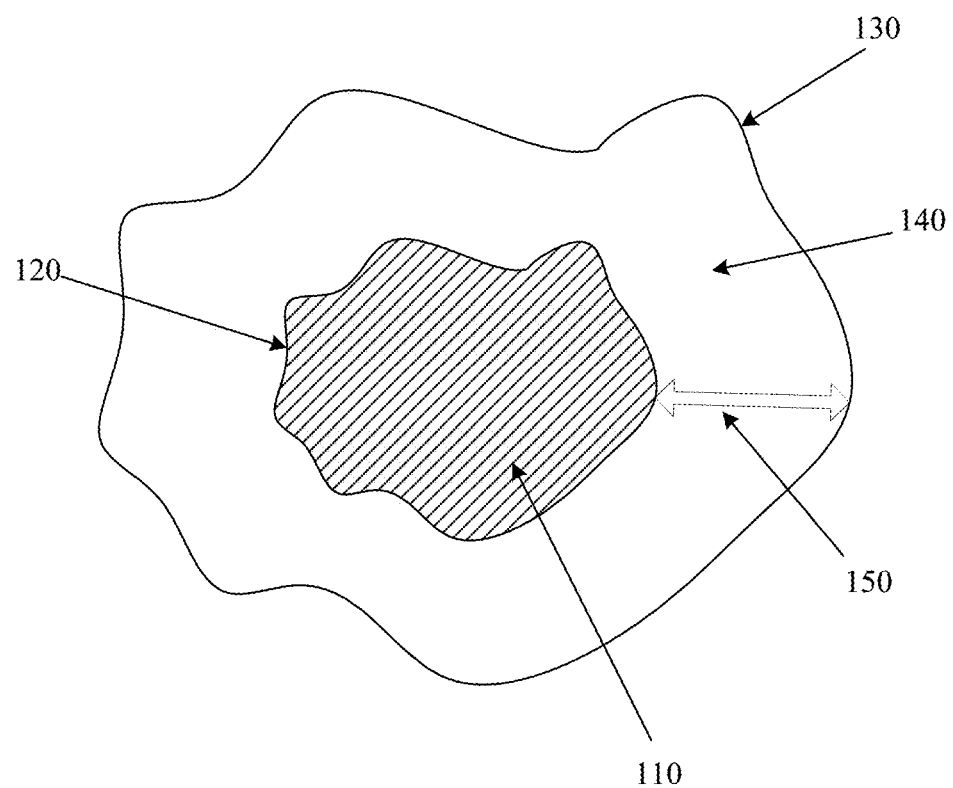
FIG. 1 illustrates an example peritumoral region.

The present disclosure will now be described with reference to the attached figures, wherein like reference numerals are used to refer to like elements throughout, and wherein the illustrated structures and devices are not necessarily drawn to scale. As utilized herein, terms "component," "system," "interface," and the like may refer to a computer-related entity, hardware, software (e.g., in execution), or firmware. For example, a component can be a processor, a process running on a processor, a controller, an object, an executable, a program, a storage device, or a computer with a processing device. By way of illustration, an application running on a server and the server can also be a component. One or more components can reside within a process, and a component can be localized on one computer or distributed between two or more computers. A set of elements or a set of other components can be described herein, in which the term "set" can be interpreted as "one or more."

Further, these components can execute from various computer readable storage media or storage devices having various data structures stored thereon such as with a module, for example. The components can communicate via local or remote processes such as in accordance with a signal having one or more data packets (e.g., data from one component interacting with another component in a local system, distributed system, or across a network, such as, the Internet, a local area network, a wide area network, or similar network with other systems via the signal).

As another example, a component can be an apparatus with specific functionality provided by mechanical parts operated by electric or electronic circuitry, in which the electric or electronic circuitry can be operated by a software application or a firmware application executed by one or more processors. The one or more processors can be internal or external to the apparatus and can execute at least a part of the software or firmware application. As yet another example, a component can be an apparatus that provides specific functionality through electronic components without mechanical parts; the electronic components can include one or more processors therein to execute software or firmware that confer(s), at least in part, the functionality of the electronic components.

Lung cancer is among the leading causes of cancer death in the world. First-line platinum-based cytotoxic chemotherapy is one approach to treating advanced NSCLC. However, first-line platinum-based cytotoxic chemotherapy produces, at best, transient responses, possibly because p53-system mutation/deletion is universal in NSCLC and metastatic disease. The immune checkpoint inhibitor (anti-PD-1) nivolumab has been employed in second-line treatment for NSCLC. Nivolumab and similar drugs have an excellent toxicity profile and may induce durable, clinically meaningful, responses in patients demonstrating NSCLC. However, the objective response rate to nivolumab therapy by patients demonstrating NSCLC is only approximately 20%. Conventional approaches to predicting response to nivolumab therapy may involve biopsies or other surgical interventions. However, biopsies are invasive procedures that are expensive, take time that may be relevant in a clinical setting, and may expose a patient to discomfort or harmful side effects. Thus, an improved approach to predicting patient response to nivolumab therapy is desirable.

Example methods and apparatus non-invasively predict nivolumab or other checkpoint inhibitor based immunotherapy response by squamous NSCLC tumors. Example embodiments predict response to nivolumab based immunotherapy using computerized analysis of radiomic features extracted from computed tomography (CT) imagery of a region of tissue demonstrating NSCLC. Radiomic features extracted from CT imagery, including texture, intensity, and shape features, involve the quantification of tumor phenotypes by using a number of automatically extracted, computerized, data-characterization approaches. Radiomic features in CT imagery cannot be accessed or extracted by pencil and paper or acquired by the human mind. Radiomic features present in CT imagery are sub-visual features that are not visible to the human eye.

Radiomic features extracted by example methods and apparatus are extracted from a tumoral region represented in a CT image and extracted from a peritumoral region represented in the CT image. A peritumoral region may be defined as the region surrounding the tumoral region out to a distance. For example, in one embodiment, the peritumoral region may be defined as the region extending 2.5 mm from the tumoral boundary. In another embodiment, the peritumoral region may be the region extending 5 mm from the tumoral boundary, or 25 mm from the tumoral boundary. The peritumoral region may be defined by a distance measured in mm, or in other units, including pixels or voxels. On pre-treatment CT, non-responders may have elevated entropy expression within the peritumoral region. Entropy may be captured by radiomic features. Textural patterns correlated with patterns of lymphocytic infiltration and vascularity may manifest at specific locations outside the tumor.

FIG. 1 illustrates an example peritumoral region 140 associated with an NSCLC tumor 110. Peritumoral region 140 is bounded by outer peritumoral boundary 130 and tumoral boundary 120. In one embodiment, example methods and apparatus morphologically dilate tumoral boundary 120 by an amount 150, resulting in the outer peritumoral boundary 130. Amount 150 may be, for example, 2.5 mm, 5 mm, 25 mm, 7 pixels, 21 pixels, or another, different amount.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where a dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary.

In one embodiment, the peritumoral region includes a plurality of annular bands. The peritumoral region may be segmented into annular bands located at varying distances from the nodule. The varying distances may be defined from the tumoral boundary, from the center of the tumor, or from other points or areas. In one embodiment, the peritumoral region is segmented into annular bands automatically. In another embodiment, the peritumoral region is segmented into annular bands manually. In one embodiment, the nodule surface is expanded to yield a set of 5 mm annular peritumoral rings of increasing distance from the nodule. In another embodiment, the annular peritumoral rings or bands may be of different widths, e.g. 2.5 mm, 5 mm, 7.5 mm, 10 mm, or 7 pixels. The width of the annular peritumoral band may be based on a property of the tumoral region, may be pre-defined, or may be selected automatically or manually. The width of the annular peritumoral band (e.g. 2.5 mm, 5 mm, 7.5 mm, 10 mm, or 7 pixels) may be selected based on an optimum discriminability associated with radiomic features extracted from the annular peritumoral band.

Figure 2:
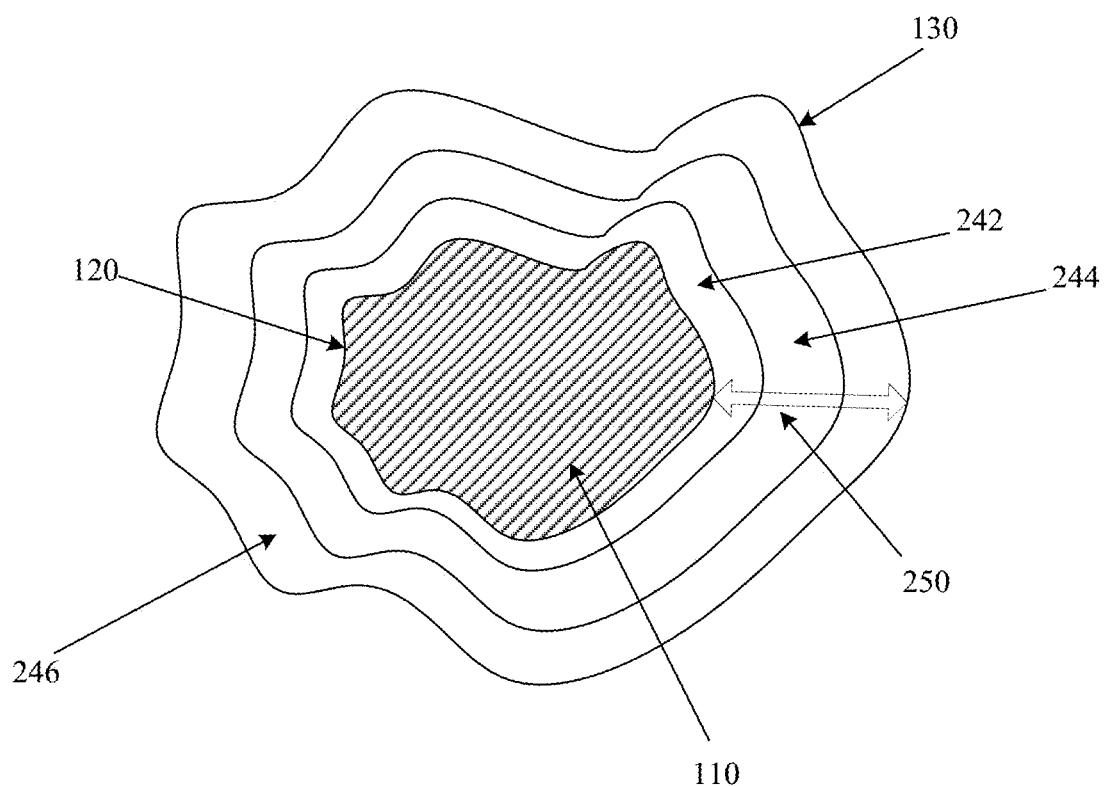
FIG. 2 illustrates an example peritumoral region with annular bands.

FIG. 2 illustrates three example annular bands in the peritumoral region of NSCLC tumor 110. Peritumoral region annular band 246 is bounded by outer peritumoral boundary 130 and annular band 244. Annular band 244 is bounded by annular band 246 and annular band 242. Annular band 242 is bounded by annular band 244 and tumoral boundary 120. In one embodiment, example methods and apparatus morphologically dilate tumoral boundary 110 by an amount 250, resulting in the outer peritumoral boundary 130. Amount 250 may be, in this example, 15 mm. Thus, in this example, annular band 242 may include the peritumoral region extending 5 mm from the tumoral boundary 120. Annular band 244 may include the peritumoral region extending 5 mm from annular band 242. Annular band 246 may include the peritumoral region extending 5 mm from annular band 244 to the peritumoral boundary 130. Other numbers of annular bands, extending different distances from the tumoral region, may be employed. For example, in one embodiment, tumoral boundary 110 may be morphologically dilated by an amount 250 that has a value of 21 pixels, and three annular bands having widths of 7 pixels respectively may be defined. While FIG. 2 is illustrated in two dimensions for clarity of illustration, the annular bands may be defined in three dimensions, and an annular band may thus encompass a peritumoral volume.

Embodiments described herein may progressively interrogate the peritumoral region. For example, one embodiment may progressively interrogate annular bands beginning with an annular band that is immediately adjacent to the tumoral region (e.g., a first annular band 242) and may extract features from first annular band 242. In this embodiment, a progressively greater number of annular bands may be interrogated (e.g. annular band 242, . . . , annular band 246), until features are extracted from a threshold number of annular bands, until a threshold level of discriminability is achieved, or until a threshold of distance from the nodule is attained. Progressively interrogating the peritumoral space in annular bands facilitates using the diagnostic contribution of features outside specific locations from the tumor boundary in predicting response to immunotherapy. For instance, the peritumoral textural features extracted by embodiments described herein may be correlated with patterns of lymphocytic infiltration and vascularity that manifest at specific locations outside the tumor. In some instances, the patterns of lymphocytic infiltration and vascularity manifest at different levels in different annular bands.

Example methods and apparatus extract radiomic features (e.g. quantitative image descriptors) from radiological images to generate predictive and prognostic information, and thus provide non-invasive biomarkers for treatment response, monitoring patients, disease prognosis, and personalized treatment planning. The extracted radiomic features are provided to a machine learning classifier. The machine learning classifier classifies the region of interest as a responder or non-responder based, at least in part, on the extracted radiomic features. Example methods and apparatus predict response to nivolumab immunotherapy in NSCLC with an area under the receiver operator characteristic (ROC) curve (AUC) of at least 0.92.

In one embodiment, a cohort of thirty-one patients who underwent lobectomy for early stage NSCLC are identified. Patients in the cohort of thirty-one patients with response to nivolumab therapy, and patients in the cohort without response to nivolumab therapy, were identified. In this example, ten responders and ten non-responders were identified. Seven patients were reserved or blinded for validation. Corresponding pre-surgical CT images associated with the responders and non-responders were accessed. The corresponding pre-surgical CT images were annotated by segmenting tumoral regions using three-dimensional (3D) slicer software. The pre-surgical CT images were further annotated by identifying a peritumoral region by morphologically dilating the tumoral region. In this example, 669 radiomic features were extracted from the tumoral region, and 732 radiomic features were extracted from the peritumoral region. The radiomic features include texture and shape features. The extracted radiomic features were evaluated and ranked according to their ability to discriminate responders from non-responders. In this example, the extracted radiomic features were evaluated and ranked using a linear discriminant analysis (LDA) machine learning classifier in terms of both univariate and multivariate analysis. The CT images associated with responders and non-responders are used to train a machine learning classifier to classify a region of tissue as a responder or non-responder. The set of validation images acquired from the set of seven blinded patients was used to test the trained classifier's performance in classifying a region of tissue as a responder or non-responder.

In this example, a set of radiomic features were extracted from the annotated tumor volumes, including the peritumoral volume. The set of radiomic features includes subvisual features that are not visible to the human eye. The set of radiomic features includes textural and shape features. Textural analysis was performed on the entire tumor volume in this example. Performing textural analysis on the entire tumor volume, or on a threshold level of tumor volume, overcomes spatial heterogeneity feature distribution across the tumor volume. In this example, a total of 669 radiomic features, including radiomic texture features and radiomic shape features, were extracted from the tumor volume. In this example, a total of 732 radiomic features were extracted from the peritumoral region. The set of radiomic texture features includes Haralick features, gray level features, gradient features, Gabor features, local binary pattern (LBP) features, Law features, and Law-Laplacian features. The set of radiomic shape features includes location features, size features, perimeter features, eccentricity features, compactness features, roughness features, elongation features, convexity features, equivalent diameter features, extension features, and sphericity features.

Figure 3:
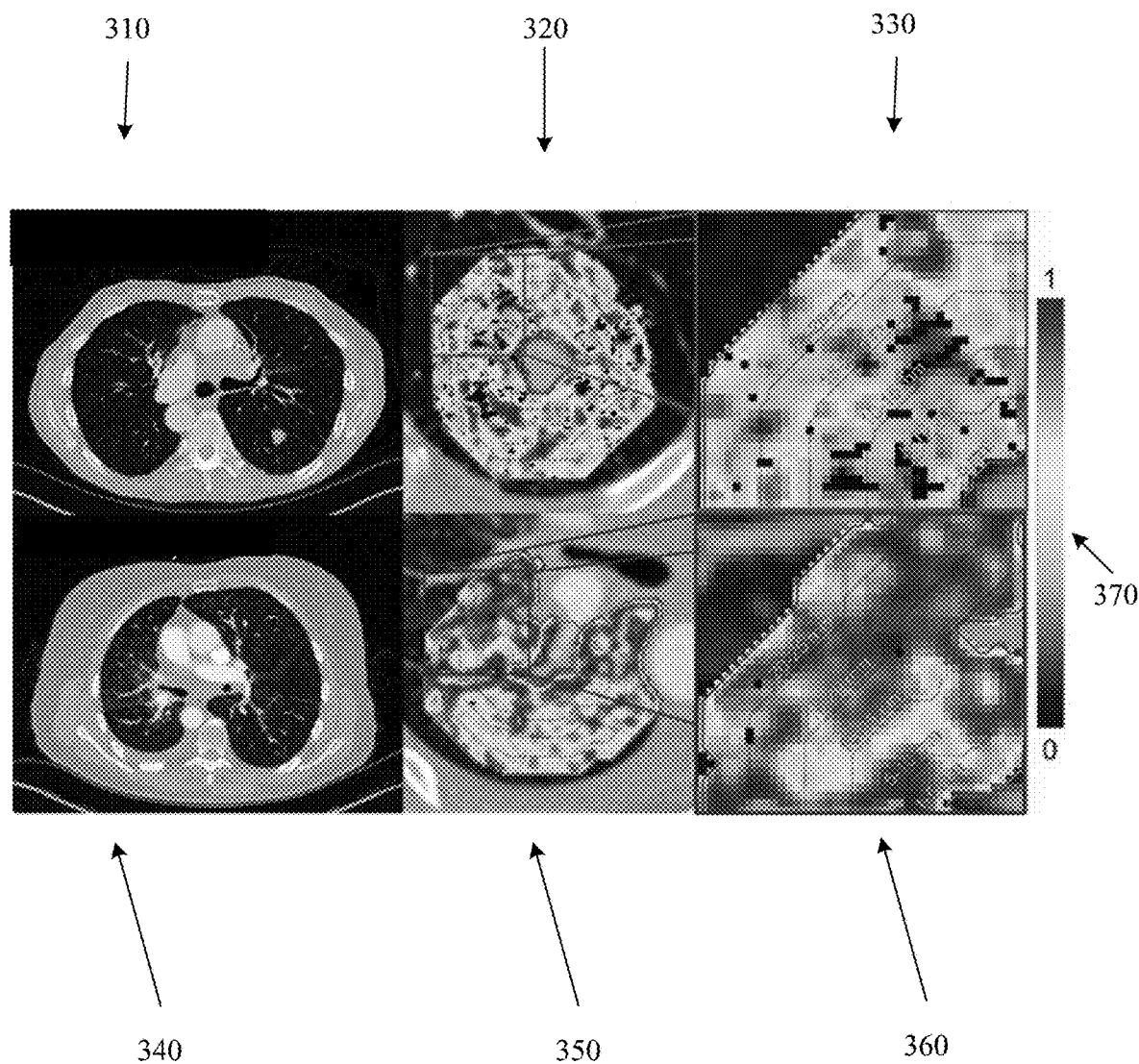
FIG. 3 illustrates example radiomic features extracted from peritumoral annular bands.

FIG. 3 illustrates a CT image of a responder nodule ROI 310 and a CT image of a non-responder ROI 340. In the example illustrated in FIG. 3, the nodular ROIs or tumoral surface for the responder nodule ROI 310 and the non-responder ROI 340 are expanded to yield a set of 5 mm annular peritumoral rings. Heatmaps 320 and 350 illustrate entropy of Haralick texture features in the perinodular zone of the responder and non-responder respectively. Close up image 330 and close up image 360 further illustrate a portion of the set of 5 mm annular peritumoral rings in the responder and non-responder respectively. A legend 370 indicates heatmap intensity.

The number of annular peritumoral rings, or the dimensions of the annular peritumoral rings (e.g. 5 mm, 2.5 mm, 10 mm, 5 pixels) may be determined based on a level of discriminability of features extracted from the annular rings. For example, a first set of features with a first level of discriminability may be extracted from a first ring at a first distance from the tumoral boundary, while a second set of features with a second, different level of discriminability may be extracted from a second, different ring at a second, different distance from the tumoral boundary. The number of annular peritumoral rings or dimensions of the annular peritumoral rings may also be determined based on a stability of a feature across different ring numbers, dimensions, or other properties. The number of annular peritumoral rings or dimensions of the annular peritumoral rings may also be based on a combination of discriminability and stability. Extracting radiomic features from an annular ring or from a set of annular rings improves the performance of a computer assisted diagnosis (CADx) system or a personalized cancer treatment system by increasing the accuracy with which response to immunotherapy is predicted. Extracting radiomic features from an annular ring or from a set of annular rings further improves the performance of a CADx system or a personalized cancer treatment system by reducing the area or volume from which radiomic features are extracted, thereby reducing the total number of radiomic features that are analyzed, and consequently reducing the computational complexity of a classification method, process, or apparatus based on extracted radiomic features. Reducing the computational complexity and number of features that need to be analyzed further improves the performance of a CADx or personalized cancer treatment system by increasing the energy efficiency of the system, and by reducing bandwidth required to access the CADx or personalized cancer treatment system.

In this example, the set of radiomic features was ranked using an LDA classifier. In one embodiment, the set of radiomic features may be ranked using a Fisher criteria score. In one embodiment, the four top ranked features were selected from the ranked features. An LDA classifier was trained using the selected radiomic features. The LDA classifier divides the feature space into two subspaces: responder to nivolumab therapy, and non-responder to nivolumab therapy. In this example, the four top ranked features selected include an entropy of Gabor feature where $S=1$, $\theta=\pi/8$, a Kurtosis of Gabor feature where $S=\frac{1}{2}$, $\theta=3\pi/8$, a Variance of Law-Laplacian L5×E5 feature, and a Variance of Gabor feature where $S=\sqrt{2}/4$, and $\theta=3\pi/8$. In this example, S represents the scale and $\theta$ represents the orientation of a normal to parallel stripes of the Gabor function. In another embodiment, other values of S and $\theta$ may be employed.

In another embodiment, the set of radiomic features is selected based on a combination of discriminability and stability across image acquisition parameters. For example, the set of radiomic features may be ranked based on the robustness of radiomic features across different segmentation approaches, slice thicknesses, reconstruction kernels, or scanner types. Discriminability for a feature may be measured as the average p-value between immunotherapy responders and non-responders. Stability may be measured as the ratio of a feature latent instability score (LI) to a preparation-induced instability score (PI). LI and PI capture feature variation within CT scans obtained from a single site or scanner, from a specific slice thickness, or reconstruction kernel. LI and PI also capture feature variation within CT scans obtained across different sites, different scanners, different reconstruction kernels, and different slice thicknesses. LI and PI further capture feature variation within CT scans obtained across different nodule segmentations, including across different annular bands, or different annular band dimensions. The most stable features will have lower LI and PI scores compared to less stable features. Example embodiments may train a machine learning classifier, including an LDA classifier or support vector machine (SVM) classifier, using a set of the most stable and discriminating features (e.g., the top three most stable and discriminating features) to predict response to immunotherapy. Variance in classifier performance for a feature over the learning set implicitly reflects feature sensitivity. Stable and discriminating features outperform discriminating features in predicting response to immunotherapy.

By increasing the accuracy with which response to nivolumab immunotherapy is predicted, example methods and apparatus produce the concrete, real-world technical effect of reducing the amount of unnecessary biopsies or other invasive procedures for patients who are unlikely to benefit from immunotherapy treatment. Additionally, example apparatus and methods reduce the expenditure of time, money and therapeutic resources on patients who are unlikely to benefit from the treatment. Example methods and apparatus thus improve on conventional approaches to predicting response to immunotherapy in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
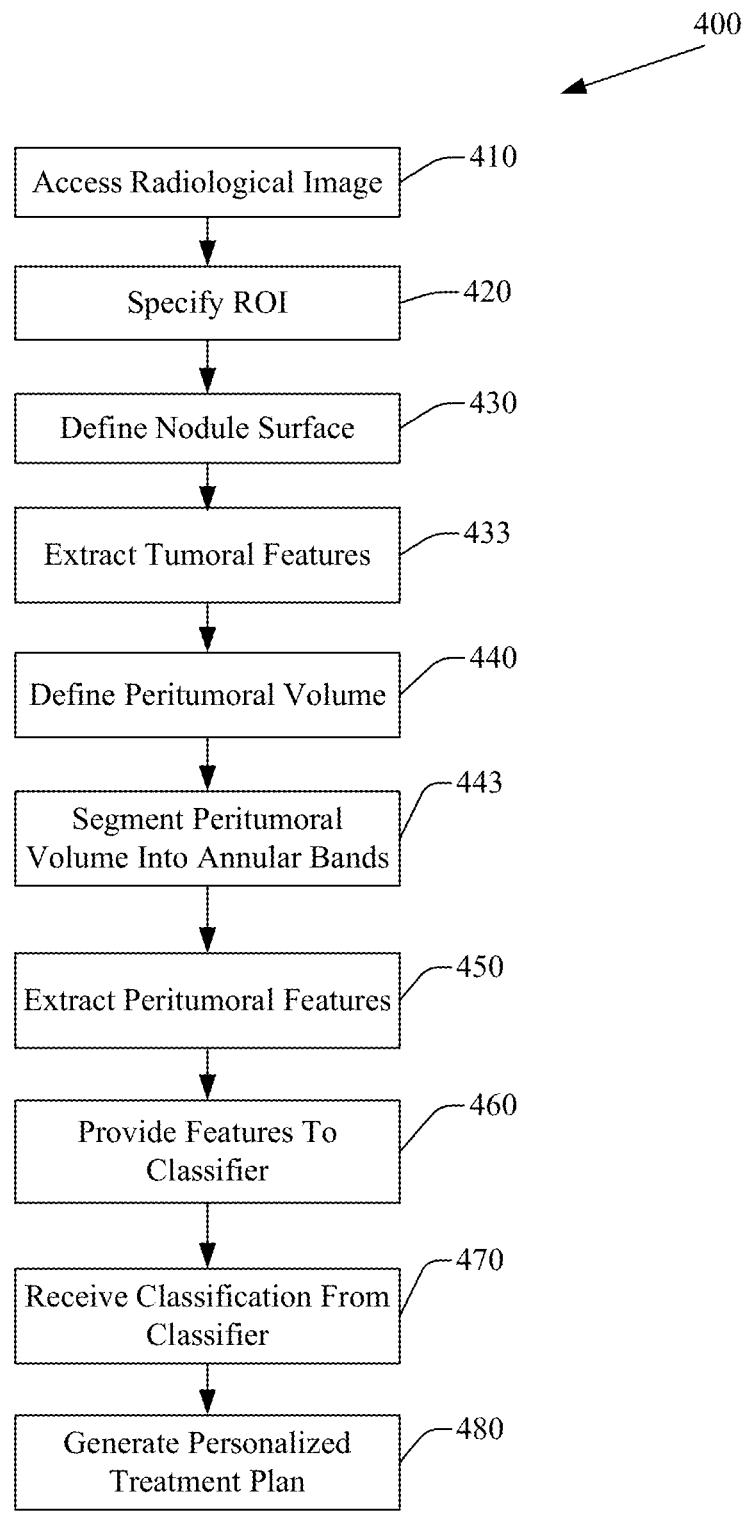
FIG. 4 illustrates an example method for predicting response to immunotherapy.

FIG. 4 illustrates an example method 400 for classifying a region of tissue, including a cancerous tumor, as a responder or non-responder. Method 400 includes, at 410, accessing a radiological image of region of tissue demonstrating cancerous pathology. The radiological image includes a plurality of pixels. In one embodiment, the radiological image is a pre-surgery CT image of a region of tissue demonstrating NSCLC. In another embodiment, the radiological image may be acquired using different imaging techniques, or may be an image of a region of tissue demonstrating a different pathology. For example, the radiological image may be an image of a region of tissue demonstrating another, different type of cancer, including melanoma, colorectal cancer, or triple-negative carcinomas.

Accessing the radiological image may include retrieving electronic data from a computer memory, receiving a computer file over a computer network, or other computer or electronic based action. Accessing the radiological image does not mean a human picking up a physical hard copy of a CT image. In one embodiment, the radiological image is acquired using a CT system. In another embodiment, other types or sizes of images may be accessed. The radiological image includes a set of morphological features. The set of morphological features includes at least a texture feature and a shape feature. In another embodiment, the set of morphological features may include an intensity feature. The set of morphological features may be extracted on a per-pixel basis, on a per-voxel basis, or using another approach.

Method 400 also includes, at 420, specifying a region of interest (ROI) represented in the image. Specifying the ROI includes annotating the ROI. In this embodiment, the ROI represents an NSCLC tumor volume. The ROI may be annotated by an expert radiologist using a 3D slicer approach, or may be annotated using an automated segmentation approach. In another embodiment, other annotation or segmentation approaches or techniques may be employed.

Method 400 also includes, at 430, defining a nodule surface based on the ROI. The nodule surface defines a tumoral volume. In one embodiment, defining the nodule surface based on the ROI includes extracting a nodule surface in three dimensions using an active contour approach. In another embodiment, the nodule surface may be defined using different approaches. For example, the nodule surface may be defined using Otzu's thresholding scheme, level set methods, or deep learning based nodule detection.

Method 400 also includes, at 433, extracting a set of discriminative tumoral features from the tumoral volume. The set of discriminative tumoral features may be extracted from a threshold volume of the ROI or tumoral volume. The set of discriminative features includes radiomic features, including an entropy of Gabor feature where $S=1$, $\theta=\pi/8$, a Kurtosis of Gabor feature where $S=\frac{1}{2}$, $\theta=3\pi/8$, a Variance of Law-Laplacian L5×E5 feature, or a Variance of Gabor feature where $S=\sqrt{2}/4$ and $theta=3\pi/8$. In another embodiment, other, different discriminative radiomic features, numbers of discriminative radiomic features, or combinations of discriminative radiomic features may be extracted. For example, the set of discriminative tumoral features may further include at least one of a Haralick feature, a gray feature, a gradient feature, a Gabor feature, an LBP feature, or a Law-Laplacian feature. The set of discriminative tumoral features may also include at least one shape feature, including at least one of a location feature, a size feature, a perimeter feature, an eccentricity feature, a compactness feature, a roughness feature, an elongation feature, a convexity feature, an equivalent diameter feature, or an extension feature.

In one embodiment, the threshold volume of the ROI or tumoral volume may be less than the total volume of the ROI. In another embodiment, the threshold volume of the ROI may be the total volume of the ROI or tumoral volume. Extracting features from the total volume of the ROI or tumoral volume overcomes spatial heterogeneity in the distribution and expression of features throughout the tumor. A threshold volume that overcomes to a clinically useful degree the spatial heterogeneity in the distribution and expression of features be employed. For example, in one embodiment, features may be extracted from ⅘ of the ROI volume rather than the total ROI volume. Employing a threshold volume that overcomes to a clinically useful degree the spatial heterogeneity in the distribution and expression of features but that includes less than the total volume of the ROI may be faster, may involve fewer computations, fewer accesses to computer memory or data storage devices, may consume less network bandwidth, or may consume less energy than performing textural analysis over the entire volume.

Method 400 also includes, at 440, defining a peritumoral volume. The peritumoral volume may be defined based on the tumoral volume. The peritumoral volume may be defined using a morphologic dilation based on the tumoral volume or the nodule surface. In one embodiment, example methods and apparatus morphologically dilate a tumoral boundary by an amount, resulting in an outer peritumoral boundary. The amount may be, for example, a distance or a number of pixels or voxels. The amount may be, for example, 2.5 mm, 5 mm, 25 mm, 7 pixels, 21 pixels, or another, different amount. The number of pixels or the distance may be determined heuristically. For example, the number of pixels or distance may be determined based on a slice thickness, on a CT system type, on a desired processing speed, on the actual size of the nodule, or on a resolution of the image. In another embodiment, the number of pixels or the distance may be selected by a user, or may be pre-defined.

In another embodiment, the peritumoral volume may be defined using other techniques or approaches. For example, the peritumoral volume may be defined as a function of a property of the tumor. The property of the tumor may include, for example, a diameter, a radius, a perimeter, an area, a volume, or other property of the tumor. The function may define the peritumoral volume or region as, for example, a morphologic dilation of the tumoral boundary or surface, where the dilation ratio is defined by a magnitude of an axis of the tumor. In another embodiment, the peritumoral volume may be defined by a disc of a threshold radius defined about the centroid of the tumor, or defined on the focal points of an elliptical representation of the tumor. In one embodiment, the peritumoral volume may be manually defined. Other approaches or combinations of approaches may be used to define the peritumoral volume.

Method 400 also includes, at 443, segmenting the peritumoral volume into a plurality of annular bands. In one embodiment, the peritumoral volume may be segmented into at least three annular bands. A member of the plurality of annular bands has a width. In one embodiment, a member of the at least three annular bands has a width of 5 mm. In another embodiment, a member of the at least three annular bands may have a width defined in pixels or voxels. For example, in an embodiment in which the peritumoral volume extends 21 pixels from the tumoral surface, the peritumoral volume may be defined into three annular bands of seven pixels each. Other embodiments may segment the peritumoral volume into other, different numbers and widths of annular bands.

Method 400 also includes, at 450, extracting a set of discriminative peritumoral features from at least one of the plurality of annular bands. The set of discriminative peritumoral features may be extracted from a threshold volume of the peritumoral volume, from a threshold number of annular bands, or from the entire peritumoral volume. Extracting the set of discriminative peritumoral features from at least one of the plurality of annular bands may include progressively interrogating the annular bands. The set of discriminative peritumoral features includes radiomic features, including an entropy of Gabor feature where $S=1$, $\theta=\pi/8$, a Kurtosis of Gabor feature where $S=\frac{1}{2}$, $\theta=3\pi/8$, a Variance of Law-Laplacian L5×E5 feature, or a Variance of Gabor feature where $S=\sqrt{2}/4$ and $theta=3\pi/8$. In another embodiment, other, different discriminative radiomic features, numbers of discriminative radiomic features, or combinations of discriminative radiomic features may be extracted from the at least one of the plurality of annular bands. For example, the set of discriminative peritumoral features may further include at least one of a Haralick feature, a gray feature, a gradient feature, a Gabor feature, an LBP feature, or a Law-Laplacian feature.

In one embodiment, the set of discriminative tumoral features or the set of discriminative peritumoral features are extracted based on a level of discriminability associated with a member of the set of discriminative tumoral features or the set of discriminative peritumoral features, and a level of stability of a member of the set of discriminative tumoral features or the set of discriminative peritumoral features. The level of stability is computed as a ratio of a feature latent instability score (LI) to a preparation-induced instability score (PI). The set of discriminative tumoral features and the set of discriminative peritumoral features may be ranked according to the level of stability, and the top N ranked feature or features may be selected, where N is an integer. Extracting the set of discriminative tumoral features and the set of discriminative peritumoral features may include retrieving electronic data from a computer memory, receiving a computer file over a computer network, or other computer or electronic based action.

Method 400 also includes, at 460, providing the set of discriminative tumoral features and the set of discriminative peritumoral features to a machine learning classifier. Providing the set of discriminative tumoral features and the set of discriminative peritumoral features may include retrieving electronic data from a computer memory, receiving a computer file over a computer network, or other computer or electronic based action. Providing the set of discriminative tumoral features and the set of discriminative peritumoral features may include providing values associated with a member of the set of discriminative tumoral features or the set of discriminative peritumoral features.

Method 400 also includes, at 470, receiving, from the machine learning classifier, a classification of the region of tissue. The machine learning classifier may classify the region of tissue as a responder or as a non-responder. The classification is based, at least in part, on the set of discriminative tumoral features and the set of discriminative peritumoral features. In one embodiment, the machine learning classifier is an LDA classifier. In another embodiment, other types of machine learning classifier, including an SVM classifier, a random forest (RF) classifier, a quadratic discriminant analysis (QDA) classifier, a K-nearest neighbors (KNN) classifier, or other type of machine learning classifier may be employed. The machine learning classifier divides the feature space into different subspaces, and classifies the region of tissue or the tumor represented by the ROI as a responder or as a non-responder. In another embodiment, the machine learning classifier computes a probability that the tumor is a responder or a non-responder.

Method 400 further includes, at 480, controlling a personalized cancer treatment system to generate a personalized treatment plan. The personalized treatment plan is based, at least in part, on the classification and the radiological image. The personalized treatment plan may include an immunotherapy recommendation, an immunotherapy schedule, an immunotherapy dosage value, a follow up treatment schedule, or other action. The personalized treatment plan may include information that facilitates developing a precision treatment plan for a patient associated with the radiological image. For example, upon determining that a tumor is classified as a responder, method 400, at 480, may control the personalized cancer treatment system to generate a first personalized treatment plan that indicates a first type of therapy, which may include nivolumab therapy. Upon determining that the tumor is classified as a non-responder, method 400, at 480, may control the personalized cancer treatment system to generate a second, different personalized treatment plan that indicates a second, different type of therapy. In another embodiment, method 400 includes, at 480, controlling a CADx system to generate a personalized treatment plan.

In one embodiment, method 400 may include training the machine learning classifier. Training the machine learning classifier may include accessing a training set of CT images of a region of tissue demonstrating NSCLC. A first subset of the training set includes an image of a region of tissue that responded to immunotherapy. A second subset of the training set includes an image of a region of tissue that did not respond to immunotherapy. A member of the training set includes a set of features. The set of features includes radiomic features, including texture features, shape features, or intensity features. The set of features may be extracted from a tumoral region represented in a member of the training set, or from a peritumoral region represented in the member of the training set. The set of features may be extracted by progressively interrogating the peritumoral region.

Training the machine learning classifier may also include selecting, from the training set, a subset of discriminative radiomic features. The subset may be selected using quadratic discriminative analysis or linear discriminant analysis. The subset may be selected as a function of an LI score and a PI score. The subset may include at least a threshold number of features. In one embodiment, the subset includes at least four features. In another embodiment, the subset may be selected using other approaches, or may include another, different number of features. For example, the subset may be selected using principal component analysis (PCA), including PCA-variable importance projection (PCA-VIP) analysis. The subset may include features that are more discriminative than other, non-selected features. A discriminative feature is a feature that demonstrates separation between different classes (e.g. responder, non-responder). Example methods and apparatus described herein may quantify a level of discriminability of a feature using, for example, a Bhattacharyya distance or other approaches. The level of discriminability may be user adjustable.

Training the machine learning classifier may also include providing the subset of discriminative features to the machine learning classifier. Providing the subset of discriminative features to the machine learning classifier may include retrieving electronic data from a computer memory, receiving a computer file over a computer network, or other computer or electronic based action. In one embodiment, the machine learning classifier is an SVM classifier. In another embodiment, the machine learning classifier is an LDA classifier, a random forest classifier, or a QDA classifier. In other embodiments, other types, combinations, or configurations of machine learning classifiers may be employed.

Training the machine learning classifier may also include accessing a testing set of CT images of a region of tissue demonstrating NSCLC. A first subset of the testing set includes an image of a region of tissue that responded to immunotherapy. A second subset of the testing set includes an image of a region of tissue that did not respond to immunotherapy. Accessing the testing set may include retrieving electronic data from a computer memory, receiving a computer file over a computer network, or other computer or electronic based action.

Training the machine learning classifier may also include testing the machine learning classifier with the testing set. Testing the machine learning classifier may include determining that the classifier has not more than a 50% false positive error rate with the second subset of the testing set, and not more than a 7% false negative error rate with the first subset of the testing set. Other false positive error rates or false negative error rates may be employed.

Figure 7:
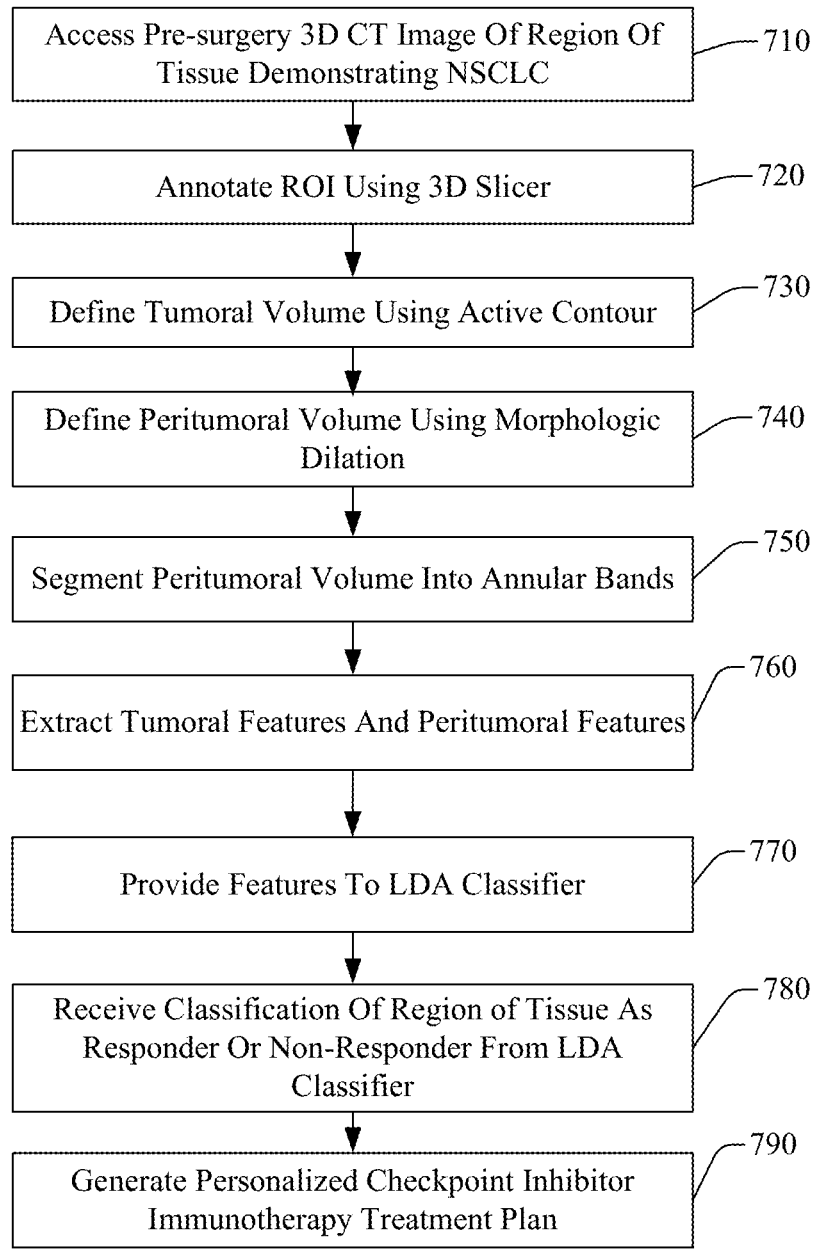
FIG. 7 illustrates a process flow of processing or generating a prediction of a response to checkpoint inhibitor immunotherapy.

While FIG. 4 illustrates various actions occurring in serial, it is to be appreciated that various actions illustrated in FIG. 4 or FIG. 7 could occur substantially in parallel. By way of illustration, a first process could access a radiological image, a second process could define a peritumoral volume, and a third process could classify a tumor as a responder or non-responder. While three processes are described, it is to be appreciated that a greater or lesser number of processes could be employed and that lightweight processes, regular processes, threads, and other approaches could be employed.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

When an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In one example, a method may be implemented as computer executable instructions. Thus, in one example, a computer-readable storage device may store computer executable instructions that if executed by a machine (e.g., computer, processor) cause the machine to perform methods described or claimed herein including method 400, or method 700. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 5:
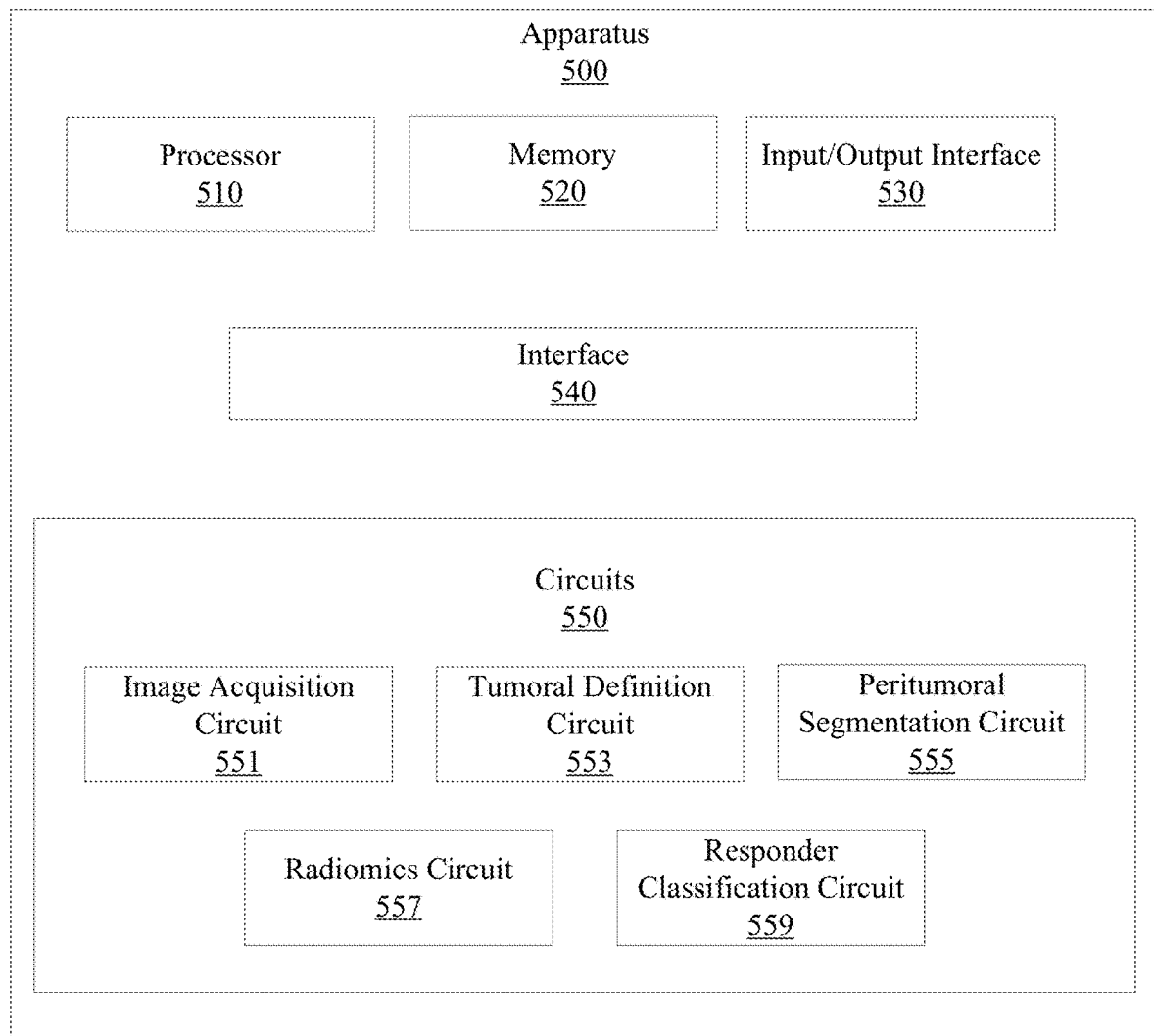
FIG. 5 illustrates an example apparatus for predicting response to immunotherapy.

FIG. 5 illustrates an example apparatus 500 for predicting response to immunotherapy in NSCLC patients. Apparatus 500 includes a processor 510, a memory 520, an input/output (I/O) interface 530, a set of circuits 550, and an interface 540 that connects the processor 510, the memory 520, the I/O interface 530, and the set of circuits 550. The set of circuits 550 includes an image acquisition circuit 551, a tumoral definition circuit 553, a peritumoral segmentation circuit 555, a radiomics circuit 557, and a responder classification circuit 559. In one embodiment, the functionality associated with the set of circuits 550 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 550 are implemented as ASICs or SOCs.

Image acquisition circuit 551 accesses a radiological image of a region of tissue demonstrating cancerous pathology. Accessing the radiological image may include retrieving electronic data from a computer memory, receiving a computer file over a computer network, or other computer or electronic based action. For example, the radiological image may be stored in memory 520. Memory 520 may include volatile memory and/or non-volatile memory. Memory 520 may be configured to store data that is accessed more frequently in faster memory, and to store data that is accessed less frequently in slower memory. For example, data associated with outer annular bands that are less frequently accessed may be stored in slower memory, while data associated with inner annular bands that are more frequently accessed may be stored in faster memory.

The radiological image has a plurality of pixels. The radiological image may be an image of a region of tissue demonstrating NSCLC. The radiological image may be a CT image that has a slice thickness, and that was acquired before the patient represented in the image was subjected to immunotherapy. The radiological image may be a member of a set of CT image slices. The radiological image includes an annotated ROI that defines a tumoral volume. The ROI has a boundary. In one embodiment, the ROI that defines the tumoral volume may be annotated on 3D slicer software by an expert radiologist. The ROI may be segmented across contiguous slices. In another embodiment, the tumoral volume may be automatically segmented. In another embodiment, other image modalities, dimensions, pixel sizes, or resolutions may also be used.

Tumoral definition circuit 553 generates a tumoral surface boundary that defines a tumoral volume. The tumoral surface boundary is based on the ROI. In one embodiment, tumoral definition circuit 553 generates the tumoral surface boundary in three dimensions using an active contour model. In another embodiment, tumoral definition circuit 553 may generate the tumoral surface boundary using other, different, approaches.

Peritumoral segmentation circuit 555 generates a peritumoral region based on the tumoral surface boundary. Peritumoral segmentation circuit 555 also segments the peritumoral region into a plurality of annular bands. In one embodiment, peritumoral segmentation circuit 555 generates the peritumoral region based on the tumoral surface boundary by defining a peri-nodular zone around the nodule surface using a morphologic dilation operation.

In one embodiment, peritumoral segmentation circuit 555 segments the peritumoral volume into at least three annular bands. In one embodiment, a member of the at least three annular bands has a width of 5 mm. In another embodiment, a member of the at least three annular bands may have a width defined in pixels or voxels. For example, in an embodiment in which the peritumoral volume extends 21 pixels from the tumoral surface, the peritumoral volume may be defined by peritumoral segmentation circuit into three annular bands having widths of seven pixels each. Other embodiments may segment the peritumoral volume into other, different numbers and widths of annular bands. The number of annular bands, or the width of an annular band, may be based on a slice thickness, on a type of CT system from which the radiological image was acquired, on a site form which the radiological image was acquired, or on another property of the radiological image.

Radiomics circuit 557 extracts a set of discriminative features from the tumoral volume and at least one of the plurality of annular bands. Radiomics circuit 557 extracts the set of discriminative features based, at least in part, on a discriminability associated with a feature, and a stability associated with the feature. In one embodiment, radiomics circuit 557 extracts the set of discriminative features based on a level of discriminability associated with a member of the set of discriminative features, and a level of stability of a member of the set of discriminative features. The level of stability is computed as a ratio of a feature latent instability score (LI) to a preparation-induced instability score (PI). The set of discriminative features may be ranked according to the level of stability, and the top ranked feature or features may be selected.

In one embodiment, the set of discriminative features may be extracted from the entire tumor volume and the entire peritumoral volume. In another embodiment, the set of discriminative features may be extracted from a threshold volume of the tumoral volume, from a threshold volume of the peritumoral volume, or from a threshold number of annular bands. The threshold number of annular bands may be, for example, one, two, three, or another, different number. Radiomics circuit 557 may progressively interrogate annular bands until discriminative features are extracted from the threshold number of annular bands. The threshold number of annular bands, threshold volume of the tumoral volume, or the threshold volume of the peritumoral volume may be based on a level of stability associated with a threshold volume or threshold number of annular bands.

The set of discriminative features may include an entropy of Gabor feature where S=1, $\theta=\pi/8$, a Kurtosis of Gabor feature where S=½, $\theta=3\pi/8$, a Variance of Law-Laplacian L5×E5 feature, or a Variance of Gabor feature where S=$\sqrt{2}/4$ and theta=$3\pi/8$. In another embodiment, other, different discriminative features, numbers of discriminative features, or combinations of discriminative features may be extracted from the tumoral volume or from the peritumoral volume. For example, the set of discriminative features may further include at least one of a Haralick feature, a gray feature, a gradient feature, a Gabor feature, an LBP feature, or a Law-Laplacian feature.

Classification circuit 559 includes a machine learning classifier that classifies the ROI as a responder or a non-responder, based, at least in part, on the set of discriminative features. The machine learning classifier may be an LDA classifier, an SVM classifier, a random forest classifier, or a QDA classifier. In another embodiment, classification circuit 559 classifies the ROI using a machine learning classifier selected from at least one of an LDA, a QDA classifier, a KNN classifier, a random forest classifier, or an SVM classifier. Classification circuit 559 may select the machine learning classifier based, at least in part, on the slice thickness, or on a stability level associated with the set of discriminative features and the machine learning classifier. Classification circuit 559 may also compute a probability that the ROI is a responder or non-responder. Classification circuit 559 generates a personalized cancer treatment plan based, at least in part, on the classification. In another embodiment, classification circuit 559 generates the personalized cancer treatment plan based on the classification or the probability, and the set of discriminative features.

Figure 6:
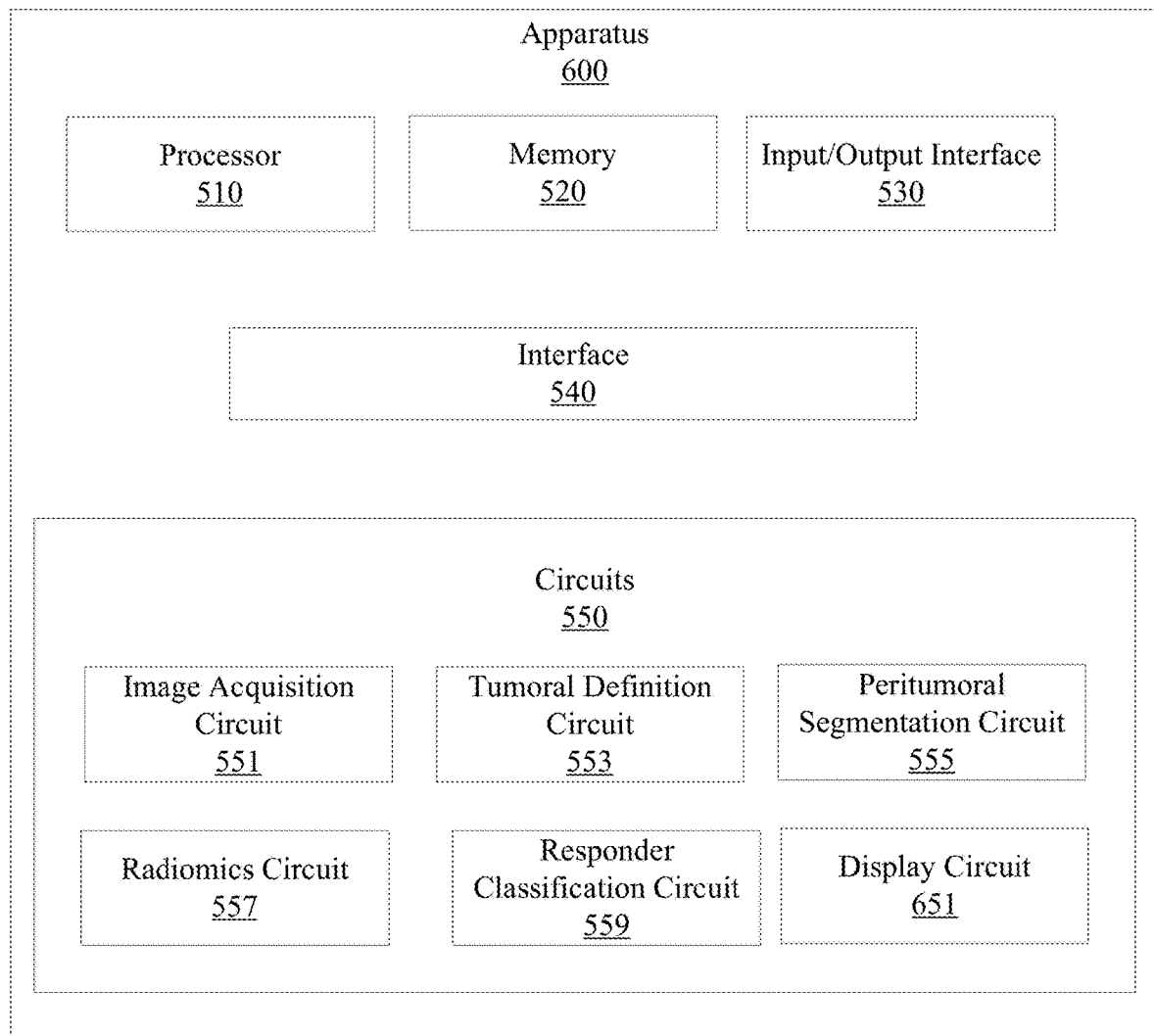
FIG. 6 illustrates an example apparatus for predicting response to immunotherapy.

FIG. 6 illustrates an example apparatus 600 that is similar to apparatus 500 but that includes additional elements and details. In one embodiment, apparatus 600 includes a display circuit 651. Display circuit 651 may control a CADx system, a CT system, a personalized cancer treatment system, or computer to display the radiological image, the discriminative features, the tumoral volume, the peritumoral volume, the annular bands, or the classification on a computer monitor, a smartphone display, a tablet display, or other displays. Displaying the image, the discriminative features, the tumoral volume, the peritumoral volume, the annular bands, or the classification may also include printing the radiological image, the discriminative features, the tumoral volume, the peritumoral volume, the annular bands, or the classification. The display circuit may also control a CADx system, a personalized cancer treatment system, or computer to display an image of the region of tissue represented by the ROI. The image of the region of tissue may include an annotated image of the ROI, or the discriminative features. By displaying the annotated image of the ROI, the classification, or the features, example apparatus provide a timely and intuitive way for a human pathologist, a personalized cancer treatment system, or a CADx system to more accurately predict response to immunotherapy, thus improving on conventional approaches to predicting response to treatment.

FIG. 7 illustrates a process flow for performing operations for predicting response to checkpoint inhibitor immunotherapy in a region of tissue demonstrating NSCLC based on radiomic features extracted from a tumoral volume and from at least one peritumoral annular band associated with the tumoral volume. A method 700 initiates at 710 with controlling at least one processor to access a set of pre-surgery non-contrast CT images of a region of tissue demonstrating NSCLC. A member of the set of CT images includes a plurality of pixels or voxels. A member of the set of CT images has a slice thickness. The processor may access the set of CT images by retrieving electronic data from a computer memory, including RAM, ROM, or other type of computer memory, by accessing a data storage device, including a hard disk drive, a solid state device, a shingled magnetic recording device, or a cloud storage system, or by receiving a computer file over a computer network, or other computer or electronic based action. Accessing the set of CT images does not mean a human picking up a physical hard copy of a CT image.

Method 700 also includes, at 720, annotating an ROI represented in the image using a 3D slicer approach. A tumor or nodule may be represented within the ROI. In another embodiment, other annotation or segmentation approaches may be employed.

Method 700 also includes, at 730, defining a tumoral or nodule surface based on the ROI. Defining the nodule surface includes extracting the nodule surface in three dimensions using an active contour approach. The nodule surface defines a tumoral volume. In another embodiment, the nodule surface may be defined using different approaches.

Method 700 also includes, at 740, defining a peritumoral volume using a morphologic dilation of the nodule surface. The morphologic dilation is based, at least in part, on a number of pixels or a distance. The number of pixels or distance may be determined heuristically. In another embodiment, the number of pixels or distance may be pre-defined, or may be user adjustable. For example, the number of pixels or distance may be determined based on a slice thickness, on a CT system type, on a desired processing speed, or on a resolution of the member of the set of CT images.

Method 700 also includes, at 750, segmenting the peritumoral volume into at least three annular bands. The dimensions of the at least three annular bands may be based, at least in part, on the number of pixels or the distance. The dimensions of the at least three annular bands may include a width. The width may be defined in pixels, voxels, mm, or other unit of measure. The width of a first annular band may be the same as the width of a second, different annular band, or the width of the first annular band may be different than the width of the second annular band. For example, in one embodiment, a first, inner annular band may have a width of 10 pixels, while a second, middle annular band may have a width of 8 pixels, and a third, outer annular band may have a width of 6 pixels. In another embodiment, the first, inner annular band may have a width of 8 pixels, the second, middle annular band has a width of 8 pixels, and the third, outer annular band also has a width of 8 pixels. In another embodiment, another function, including a Gaussian or exponential, may be used to modulate the width of the peri-tumoral rings emanating from the surface of the nodule. In another embodiment, the dimensions of the at least three annular bands are determined in relation to a centroid of the tumoral volume.

Method 700 also includes, at 760, extracting a set of tumoral features from the tumoral volume, and extracting a set of peritumoral features from at least one of the at least three annular bands. The set of tumoral features and the set of peritumoral features are selected as a function of a level of discriminability associated with a member of the set of tumoral features or the set of peritumoral features, and a level of stability of a member of the set of tumoral features or the set of peritumoral features. The level of stability of the member of the set of tumoral features or the level of stability of the member of the set of peritumoral features is based, at least in part, on the slice thickness. In one embodiment, a level of stability is computed as a ratio of an LI score to a PI score. The set of tumoral features and the set of peritumoral features may be ranked according to the level of stability, and the top ranked feature or features may be selected.

The set of tumoral features and the set of peritumoral features include an entropy of Gabor feature where $S=1$, $\theta=\pi/8$, a Kurtosis of Gabor feature where $S=\frac{1}{2}$, $\theta=3\pi/8$, a Variance of Law-Laplacian L5×E5 feature, and a Variance of Gabor feature where $S=\sqrt{2}/4$ and $theta=3\pi/8$. In another embodiment, the set of tumor features and the set of peri-tumoral features may include other, different radiomic features, including texture features, shape features, or intensity features.

Method 700 also includes, at 770, providing the set of tumoral features and the set of peritumoral features to an LDA machine learning classifier. Providing the set of tumoral features and the set of peritumoral features may include retrieving electronic data from a computer memory, receiving a computer file over a computer network, or other computer or electronic based action.

Method 700 also includes, at 780, receiving, from the LDA machine learning classifier, a classification of the region of tissue as a responder to checkpoint inhibitor immunotherapy or as a non-responder to checkpoint inhibitor immunotherapy. The classification is based on the set of tumoral features and the set of peritumoral features. The classification may include a probability that the region of tissue is a responder or non-responder. Receiving the classification may include retrieving electronic data from a computer memory, receiving a computer file over a computer network, or other computer or electronic based action.

Method 700 further includes, at 790, generating (e.g. the at least one processor generates) a personalized checkpoint inhibitor immunotherapy treatment plan. The personalized checkpoint inhibitor immunotherapy treatment plan is based, at least in part, on the classification. The personalized checkpoint inhibitor immunotherapy treatment plan includes an immunotherapy recommendation, an immunotherapy dosage value, or an immunotherapy schedule. Method 700 may further include controlling the at least one processor to display the classification, the prediction, the ROI, the personalized checkpoint inhibitor immunotherapy treatment plan, or the set of pre-surgery non-contrast CT images on a on a computer monitor, a smartphone display, a tablet display, or other displays.

Figure 8:
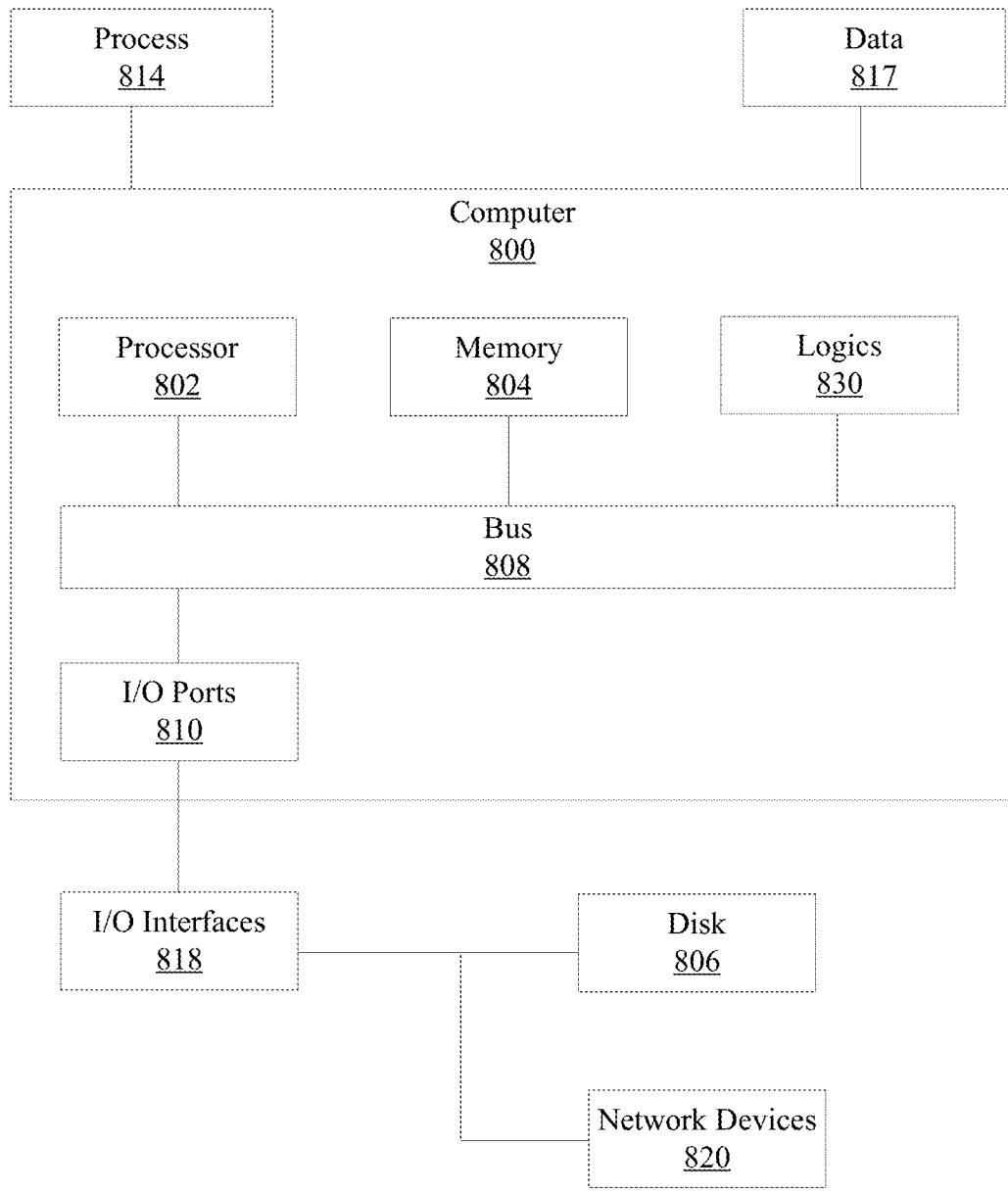
FIG. 8 illustrates an example computer in which example methods, processes, and apparatus may operate.

FIG. 8 illustrates an example computer 800 in which example methods and processes described herein can operate and in which example circuits or logics may be implemented. In different examples, computer 800 may be part of a CT system, a digital whole slide scanner, may be operably connectable to a digital whole slide scanner system or CT system, or may be part of an automated tissue grading system, a personalized cancer treatment system, or a CADx system.

Computer 800 includes a processor 802, a memory 804, and input/output ports 810 operably connected by a bus 808. In one example, computer 800 may include a set of logics 830 that perform a method (e.g. method 400, method 700) of predicting NSCLC patient response to immunotherapy. Thus, the set of logics 830, whether implemented in computer 800 as hardware, firmware, software, and/or a combination thereof may provide means (e.g., hardware, software) for predicting NSCLC patient response to immunotherapy. In different examples, the set of logics 830 may be permanently and/or removably attached to computer 800. In one embodiment, the functionality associated with the set of logics 830 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 830 are implemented as ASICs or SOCs.

Processor 802 can be a variety of various processors including dual microprocessor and other multi-processor architectures. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a solid state device (SSD), a flash memory card, or a memory stick. Furthermore, disk 806 may include optical drives like a CD-ROM or a digital video ROM drive (DVD ROM). Memory 804 can store processes 814 or data 817, for example. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, logics, and peripherals using other busses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, a CT system, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks. In one embodiment, computer 800 may be a part of or may interact with a cloud data storage system. For example, a set of pre-surgery CT images may be stored in a cloud data storage system, and may be accessed by example methods and apparatus.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer control the computer to perform a method for predicting response to immunotherapy, the method comprising:
    accessing a radiological image of a region of tissue demonstrating cancerous pathology, where the radiological image includes a plurality of voxels;
    specifying a region of interest (ROI) in the image;
    defining a nodule surface based on the ROI, where the nodule surface defines a tumoral volume;
    extracting a set of discriminative tumoral features from the tumoral volume;
    defining a peritumoral volume using a morphologic dilation based on the tumoral volume;
    segmenting the peritumoral volume into a plurality of annular bands;
    extracting a set of discriminative peritumoral features from at least one of the plurality of annular bands;
    providing the set of discriminative tumoral features and the set of discriminative peritumoral features to a machine learning classifier;
    receiving, from the machine learning classifier, a classification of the region of tissue, where the classification is based on the set of discriminative tumoral features and the set of discriminative peritumoral features; and
    controlling a personalized cancer treatment system to generate a personalized treatment plan based, at least in part, on the classification, where the personalized treatment plan includes an immunotherapy recommendation, an immunotherapy dosage value, or an immunotherapy schedule,
    where the set of discriminative tumoral features or the set of discriminative peritumoral features are extracted based on a level of discriminability associated with a member of the set of discriminative tumoral features or the set of discriminative peritumoral features, and a level of stability of a member of the set of discriminative tumoral features or the set of discriminative peritumoral features.

2. The non-transitory computer-readable storage device of claim 1, where the radiological image is a pre-surgery three-dimensional (3D) computed tomography (CT) image of a region of tissue demonstrating non-small cell lung cancer (NSCLC).

3. The non-transitory computer-readable storage device of claim 2, where specifying the ROI includes annotating the image using a 3D slicer approach.

4. The non-transitory computer-readable storage device of claim 1 where defining a nodule surface based on the ROI includes extracting a nodule surface in three dimensions using an active contour approach.

5. The non-transitory computer-readable storage device of claim 1, where defining the peritumoral volume using a morphologic dilation based on the tumoral volume includes defining the peritumoral volume using a morphologic dilation based on the nodule surface.

6. The non-transitory computer-readable storage device of claim 5, where the peritumoral volume is defined based on a morphologic dilation based on the nodule surface, and by one of a number of pixels or a distance.

7. The non-transitory computer-readable storage device of claim 6, where the number of pixels or the distance is determined heuristically.

8. The non-transitory computer-readable storage device of claim 6, where the distance is 25 mm.

9. The non-transitory computer-readable storage device of claim 6, where segmenting the peritumoral volume into a plurality of annular bands includes segmenting the peritumoral volume into at least three annular bands.

10. The non-transitory computer-readable storage device of claim 9, where a member of the at least three annular bands has a width of 5 mm.

11. The non-transitory computer-readable storage device of claim 1, where the level of stability is computed as a ratio of a feature latent instability score (LI) to a preparation-induced instability score (PI).

12. The non-transitory computer-readable storage device of claim 11, where the set of discriminative tumoral features or the set of discriminative peritumoral features includes an entropy of Gabor feature where $S=1$, $\theta=\pi/8$, a Kurtosis of Gabor feature where $S=1/2$, $\theta=3\pi/8$, a Variance of Law-Laplacian L5×E5 feature, and a Variance of Gabor feature where $S=\sqrt{2}/4$ and $\theta=3\pi/8$.

13. The non-transitory computer-readable storage device of claim 1, where the machine learning classifier is a linear discriminant analysis (LDA) classifier, a support vector machine (SVM), a quadratic discriminant analysis (QDA) classifier, or a random forest classifier.

14. The non-transitory computer-readable storage device of claim 1, the method further comprising training the machine learning classifier using a training set of CT images of a region of tissue demonstrating cancerous pathology, and a testing set of CT images of a region of tissue demonstrating cancerous pathology.

15. An apparatus for predicting response to immunotherapy, comprising:
a processor;
a memory that stores a set of radiological images of a region of tissue demonstrating cancerous pathology;
an input/output interface;
a set of circuits, where the set of circuits includes an image acquisition circuit, a tumoral definition circuit, a peritumoral segmentation circuit, a radiomics circuit, and a classification circuit; and
an interface that connects the processor, the memory, the input/output interface, and the set of circuits:
where the image acquisition circuit accesses a radiological image from among the set radiological images of a region of tissue demonstrating cancerous pathology, where the radiological image has a plurality of pixels, and where the radiological image includes an annotated region of interest (ROI);
where the tumoral definition circuit generates a tumoral surface boundary that defines a tumoral volume, based on the ROI;
where the peritumoral segmentation circuit generates a peritumoral region based on the tumoral surface boundary, and that segments the peritumoral region into a plurality of annular bands;
where the radiomics circuit extracts a set of discriminative features from the tumoral volume and at least one of the plurality of annular bands based, at least in part, on a discriminability associated with a feature, and a stability associated with the feature; and
where the classification circuit includes a machine learning classifier that classifies the ROI as a responder or a non-responder, based, at least in part, on the set of discriminative features, where the machine learning classifier is a linear discriminant analysis (LDA) classifier, a support vector machine (SVM) classifier, a random forest classifier, or a quadratic discriminant analysis (QDA) classifier.

16. The apparatus of claim 15, where the tumoral definition circuit generates the tumoral surface boundary in three dimensions using an active contour model.

17. The apparatus of claim 16, where the peritumoral segmentation circuit generates the peritumoral region based on the tumoral surface boundary by defining a peri-nodular zone around the tumoral surface using a morphologic dilation operation, and where the peritumoral segmentation circuit segments the peri-nodular zone into a plurality of annular bands.

18. The apparatus of claim 17 where the set of discriminative features includes an entropy of Gabor feature where $S=1$, $\theta=\pi/8$, a Kurtosis of Gabor feature where $S=1/2$, $\theta=3\pi/8$, a Variance of Law-Laplacian L5×E5 feature, and a Variance of Gabor feature where $S=\sqrt{2}/4$ and $\theta=3\pi/8$.

19. A computer-readable storage device storing executable instructions that, in response to execution, cause one or more processors of a personalized cancer treatment system to perform operations comprising:
accessing a set of pre-surgery three-dimensional (3D) computed tomography (CT) images of a region of tissue demonstrating non-small cell lung cancer (NSCLC), where a member of the set of CT images includes a plurality of pixels, and where a member of the set of CT images has a slice thickness;
annotating a region of interest (ROI) in the image using a 3D slicer approach;
defining a nodule surface based on the ROI by extracting the nodule surface in three dimensions using an active contour approach, where the nodule surface defines a tumoral volume;
defining a peritumoral volume using a morphologic dilation of the nodule surface, where the morphologic dilation is based, at least in part, on a number of pixels or a distance, where the number of pixels or distance is determined heuristically;
segmenting the peritumoral volume into at least three annular bands;
extracting a set of tumoral features from the tumoral volume, and extracting a set of peritumoral features from at least one of the at least three annular bands, based on a level of discriminability associated with a member of the set of tumoral features or the set of peritumoral features, and a level of stability of a member of the set of tumoral features or the set of peritumoral features, where the level of stability of the member of the set of tumoral features or the level of stability of the member of the set of peritumoral features is based, at least in part, on the slice thickness, and where the set of tumoral features and the set of peritumoral features include an entropy of Gabor feature where $S=1$, $\theta=\pi/8$, a Kurtosis of Gabor feature where $S=1/2$, $\theta=3\pi/8$, a Variance of Law-Laplacian L5×E5 feature, and a Variance of Gabor feature where $S=\sqrt{2}/4$ and $\theta=3\pi/8$;
providing the set of tumoral features and the set of peritumoral features to a linear discriminant analysis (LDA) machine learning classifier;
receiving, from the LDA machine learning classifier, a classification of the region of tissue as a responder to checkpoint inhibitor immunotherapy or as a non-responder to checkpoint inhibitor immunotherapy, where the classification is based on the set of tumoral features and the set of peritumoral features; and
generating a personalized checkpoint inhibitor immunotherapy treatment plan based, at least in part, on the classification, where the personalized immunotherapy treatment plan includes an immunotherapy recommendation, an immunotherapy dosage value, or an immunotherapy schedule.

* * * * *

UNITED STATES PATENT AND TRADEMARK OFFICE
CERTIFICATE OF CORRECTION

| | | |
|---|---|---|
| PATENT NO. | : 10,950,351 B2 | Page 1 of 1 |
| APPLICATION NO. | : 16/251214 | |
| DATED | : March 16, 2021 | |
| INVENTOR(S) | : Anant Madabhushi et al. | |

It is certified that error appears in the above-identified patent and that said Letters Patent is hereby corrected as shown below:

In the Specification

Column 1, Line 14; please add the following federal funding notice:
--This invention was made with government support under grants CA179327, CA195152, DK098503, CA199374, CA202752, CA208236, and RR012463 awarded by the National Institutes of Health; and grants W81XWH-16-1-0329, W81XWH-14-1-0323, W81XWH-13-1-0418, and W81XWH-15-1-0558 awarded by the Department of Defense. The government has certain rights in the invention.--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*